United States Patent
Shahrjerdi et al.

(10) Patent No.: US 11,946,895 B2
(45) Date of Patent: Apr. 2, 2024

(54) ENGINEERING CARBON-BASED STRUCTURES FOR SENSING APPLICATIONS

(71) Applicant: NEW YORK UNIVERSITY, New York, NY (US)

(72) Inventors: Davood Shahrjerdi, New York, NY (US); Roozbeh Kiani, New York, NY (US); Ting Wu, New York, NY (US)

(73) Assignee: NEW YORK UNIVERSITY, New York, NY (US)

( * ) Notice: Subject to any disclaimer, the term of this patent is extended or adjusted under 35 U.S.C. 154(b) by 913 days.

(21) Appl. No.: 16/635,634

(22) PCT Filed: Jul. 31, 2018

(86) PCT No.: PCT/US2018/044534
§ 371 (c)(1),
(2) Date: Jan. 31, 2020

(87) PCT Pub. No.: WO2019/027975
PCT Pub. Date: Feb. 7, 2019

(65) Prior Publication Data
US 2021/0131994 A1    May 6, 2021

Related U.S. Application Data

(60) Provisional application No. 62/539,045, filed on Jul. 31, 2017, provisional application No. 62/599,303, filed on Dec. 15, 2017.

(51) Int. Cl.
*H01B 1/04* (2006.01)
*G01N 27/00* (2006.01)
(Continued)

(52) U.S. Cl.
CPC ..... *G01N 27/308* (2013.01); *G01N 33/48707* (2013.01); *H01B 1/04* (2013.01)

(58) Field of Classification Search
CPC .......... H01B 1/00; H01B 1/04; C01B 32/182; G01N 27/308
See application file for complete search history.

(56) References Cited

U.S. PATENT DOCUMENTS

| | | | |
|---|---|---|---|
| 2012/0063529 A1* | 3/2012 | Choi | H04L 25/021 375/267 |
| 2012/0212242 A1 | 8/2012 | Masel et al. | |

(Continued)

FOREIGN PATENT DOCUMENTS

| | | |
|---|---|---|
| WO | WO 2011/004136 A1 | 1/2011 |
| WO | WO 2017/060497 A1 | 4/2017 |

OTHER PUBLICATIONS

Borysiuk et al "Structural defects in epitaxial graphene layers synthesized on C-terminated 4H-SiC ( ) surface—Transmission electron microscopy and density functional theory studies", Journal of Applied Physics 115, 054310 (2014).*

(Continued)

*Primary Examiner* — Mark Kopec
(74) *Attorney, Agent, or Firm* — Scully, Scott, Murphy & Presser, P.C.

(57) ABSTRACT

Principles for reliable manufacturing carbon-based electrodes with arbitrary sensitivity and homogeneity are provided. Specifically, the sensitivity of carbon-based electrodes can be engineered by changing the density of $sp^2$ type defects present in a multilayer graphene film. The engineered carbon-based electrodes can be used as a passive sensing element in electrochemical measurement of a target analyte. Carbon-based electrodes are also disclosed that have $sp^2$ hybridization and can include multilayer graphene films. The disclosed carbon-based electrodes have a density (Continued)

of zero-dimensional defects (i.e., point-like defects) which provides enhanced area-normalized sensitivity when used in sensing applications. The maximum area-normalized sensitivity is achieved at the point defect density of $4\text{-}5 \times 10^{12}$ cm$^{-2}$.

9 Claims, 11 Drawing Sheets

(51) Int. Cl.
  *G01N 27/30* (2006.01)
  *G01N 33/487* (2006.01)

(56) References Cited

U.S. PATENT DOCUMENTS

| | | | |
|---|---|---|---|
| 2012/0288750 A1* | 11/2012 | Kung | B82Y 30/00 977/734 |
| 2014/0209480 A1 | 7/2014 | Cheng et al. | |
| 2015/0221474 A1* | 8/2015 | Bedworth | B01D 69/12 250/251 |
| 2019/0330064 A1* | 10/2019 | Tour | B01D 71/021 |

OTHER PUBLICATIONS

Gass et al "Free-standing graphene at atomic resolution", Nature Nanotechnology, vol. 3, Nov. 2008 (pp. 676-681).*
Thiyagarajan et al "Defect-induced metallic-to-semiconducting transition in multilayer graphene", RSC Adv., 2015, 5, 16821.*
Banhart et al "Structural Defects in Graphene", ACS Nano, vol. 5, No. 1, pp. 26-41.*
Patil et al "Effect of plasma treatment on multilayer graphene: X-ray photoelectron spectroscopy, surface morphology investigations and work function measurements", RSC Adv., 2016, 6, 48843.*
International Search Report dated Oct. 17, 2018 issued in PCT/US2018/044534.
Banhart, Florian et al., "Structural Defects in Graphene", ACS Nano (2011), vol. 5, No. 1, pp. 26-41.
Kannan, Padmanathan Karthick et al., "Highly sensitive and selective electrochemical dopamine sensing properties of multilayer graphene nanobelts", Nanotechnology (2016), vol. 27, pp. 1-9.
Terrones, Humberto et al., "The role of defects and doping in 2D graphene sheets and 1D nanoribbons", Reports on Progress in Physics (2012), 062501, vol. 75, pp. 1-30.

\* cited by examiner

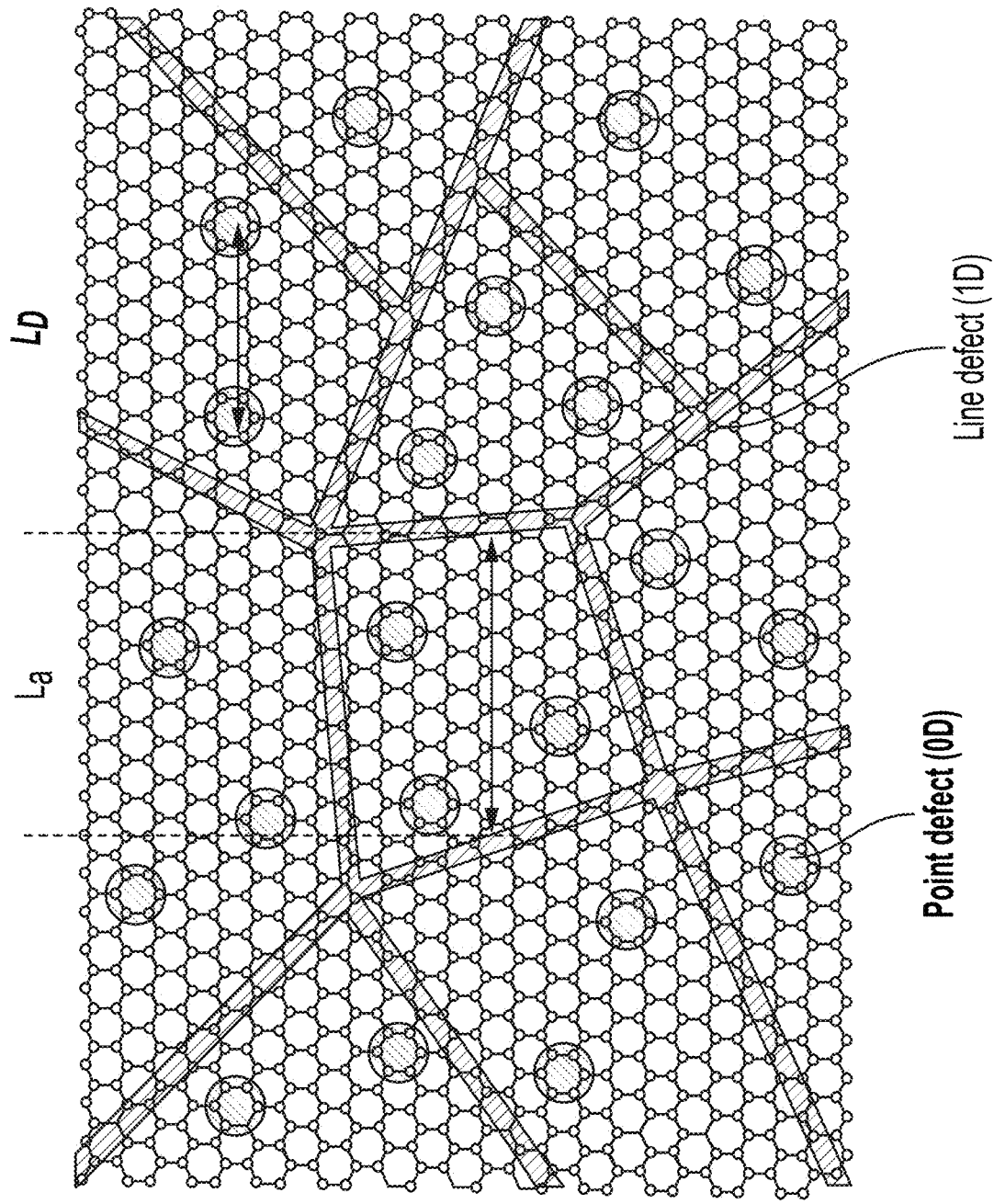

ENGINEERING CARBON-BASED STRUCTURES FOR SENSING APPLICATIONS

RELATED APPLICATIONS

This application claims benefit of U.S. Provisional Application Ser. No. 62/539,045, filed Jul. 31, 2017, and U.S. Provisional Application Ser. No. 62/599,303, filed Dec. 15, 2017, the entire contents and disclosures of which are incorporated herein by reference.

STATEMENT REGARDING FEDERALLY SPONSORED RESEARCH OR DEVELOPMENT

Part of the invention was made with government support under grant number DE-SC0012704 awarded by the Department of Energy and grant number NSF-CMMI award 1728051 awarded by the National Science Foundation. The government has certain rights in the invention.

FIELD OF THE INVENTION

The present disclosure relates to engineered structures for manufacturing reproducible and reliable carbon-based sensors with enhanced sensitivity, and to methods of forming such engineered structures. The present disclosure further relates to a method of using such carbon-based sensors for various sensing applications. The present disclosure also relates to carbon-based electrodes containing graphitic or graphene-like films having a density of a specific type of structural defects which provide enhanced area-normalized sensitivity when used in sensing applications. Since the disclosed principles are similarly applicable to both "graphene-like" and "graphitic" electrodes, these two terms are interchangeable throughout this disclosure, unless otherwise is stated.

BACKGROUND

Carbon-based electrodes have been pervasively employed as passive sensing elements in electrochemistry, where electrodes undergo redox reactions with target analytes, producing a measurable current signal. The amplitude of this current and its variation with the applied potential can provide information about the type and concentration of analytes. Voltammetry and amperometry are prime examples of such electrochemical measurements in which sensors containing carbon-based electrodes can be used. Although electrochemical sensing methods are diverse, the disclosed sensor structures in this application are applicable to all those methods.

To teach the material structures and production methods disclosed in this application for accurately tuning the sensitivity of carbon-based sensors, a fast scan cyclic voltammetry (FSCV) is used herein as an example electrochemical sensing method. FSCV is a variant of voltammetry suitable for measuring analytes in chemically complex environments with high measurement noise, such as the brain. FSCV offers good ionic specificity, high sensitivity, and sub-second detection resolution. As a result, FSCV has been a method of choice for measuring dopamine, a crucial neurotransmitter for action-selection and reward-motivated behavior that is implicated in several pathological conditions including, drug addiction, Schizophrenia, and Parkinson's disease.

FSCV measurements of dopamine have been commonly performed with cylindrical carbon fiber (CF) electrodes. Past studies have also utilized carbon-based electrodes composed of planar pyrolyzed carbon and carbon nanotubes for FSCV detection of dopamine. Pyrolyzed carbon exhibits comparable sensitivity to existing CF electrodes. Carbon nanotubes are rolled sheets of $sp^2$-bonded carbon atoms that have good sensitivity and rapid electron transfer kinetics during FSCV measurement of dopamine.

Although these forms of carbon have been used as electrochemical sensors, the physical principles that give them good sensitivity are largely unknown. Understanding these principles may make it possible to systemically engineer enhanced carbon-based sensors with high sensitivity, reproducibility and homogeneity.

Beyond neuromodulators, carbon-based electrochemical sensors have vast utility for measuring a variety of biological and chemical compounds that are important for applications such as drug development, clinical diagnostics, etc. Among different forms of carbon, electrodes made from $sp^2$-bonded carbon materials (e.g., carbon nanotubes, graphene, and reduced graphene oxide) have shown high electrode sensitivity. High sensitivity of these carbon materials is often speculated to be due to the presence of structural defects (e.g., edge plane sites) or oxygen-containing functional groups.

However, a quantitative understanding of how structural properties of a carbon-based electrode material affect the electrode sensitivity is currently unavailable. Hence, no model yet exists for accurate tuning of the electrode sensitivity by engineering the structural properties of the electrode material. Quantifying the specific role of different defects in amplifying the sensitivity of carbon materials is crucial for developing such a model.

SUMMARY

The present disclosure teaches the quantitative relationships between structural defects in graphene-based materials and the electrode sensitivity, which are the basis for developing a predictive model. These quantitative principles provide a practical guide for manufacturing engineered carbon-based sensors with enhanced sensitivity. The resulting sensors not only can achieve a desired sensitivity, but also will have homogeneous sensitivities. Specifically, it has been determined that the area-normalized sensitivity of sensors in the stage (i) of the graphene amorphization trajectory increases in linear proportion to the average density of point defects and it is unaffected by the average density of line defects and oxygen-containing functional groups. The area-normalized sensitivity drops upon transition into the stage (ii) of the graphene amorphization trajectory.

The engineered carbon-based electrodes of the present disclosure can be used as a passive sensing element in electrochemistry. In some embodiments, the engineered carbon-based electrodes of the present disclosure can be used in FSCV for sub-second measurement of the concentration of dopamine molecules.

In one aspect of the present disclosure, a carbon-based sensor is provided that includes carbon-based electrodes that are composed of multilayered graphene having engineered $sp^2$ type defects. Stated in other terms, the carbon-based sensor includes an electrode composed of a vertical stack of graphene crystals, wherein each graphene crystal of the vertical stack contains two-dimensional chains of aromatic carbon rings in which the carbon atoms are $sp^2$ hybridized.

The vertical stacking of the individual graphene layers across the film can be either fully ordered or turbostratic (local vertical ordering).

Another aspect of the present disclosure relates to a method for electrochemical analysis of a targeted analyte. In one embodiment, the method may include providing a carbon-based sensor comprising an electrode composed of multilayer graphene containing engineered $sp^2$ type defect sites. The density of these defects changes the sensitivity of the electrodes. A targeted analyte is then brought into contact with the carbon-based sensor, and thereafter, a signal generated by an electrochemical reaction of the targeted analyte at the electrode surface is detected.

The present disclosure further provides carbon-based electrodes containing graphene-like films having a density of zero-dimensional defects (e.g., defects due to atomic vacancies in the carbon lattice) which provide enhanced area-normalized sensitivity when used in sensing applications. Zero-dimensional defects may also be referred to herein as "point defects" or "point-like defects". The graphene-like films that can be employed in the present disclosure have $sp^2$ hybridization. By "$sp^2$ hybridization" it is meant that the 2s orbital of a carbon atom mixes with two of the three available $2p$ orbitals to create new hybrid orbitals that form chemical bonds between atoms (e.g., between carbon atoms in graphene).

In accordance with an aspect of the present disclosure, a carbon-based electrode is provided. In one embodiment of the present disclosure, the carbon-based electrode is composed of a graphene-like film having $sp^2$ hybridization and containing a density of zero-dimensional defects and one-dimensional defects.

In another embodiment, the carbon-based electrode is composed of a fully disordered $sp^2$ carbon material and containing a density of zero-dimensional defects and one-dimensional defects.

In accordance with another aspect of the present disclosure, a carbon-based sensor is provided. In one embodiment of the present disclosure, the carbon-based sensor includes an electrode composed of a $sp^2$ hybridized carbon film in stage (i) or (ii) of the graphene amorphization trajectory and containing a density of zero-dimensional defects.

In accordance with a further aspect of the present disclosure, a method for electrochemical analysis of a targeted analyte is provided. In one embodiment, the method may include providing a carbon-based sensor comprising an electrode composed of a $sp^2$ hybridized carbon film in stage (i) or (ii) of the graphene amorphization trajectory and containing a density of zero-dimensional defects. Next, the targeted analyte is brought into contact with the carbon-based sensor. A signal generated by an electrochemical reaction of the targeted analyte at a surface of the electrode is detected.

BRIEF DESCRIPTION OF SEVERAL VIEWS OF THE DRAWINGS

FIG. 3A shows the schematic illustration of graphene containing point and line defects. The density of the point defects can be quantified from the average distance between them ($L_D$). The average crystallite size ($L_a$) represents the density of line defects.

DETAILED DESCRIPTION

Figure 1A:
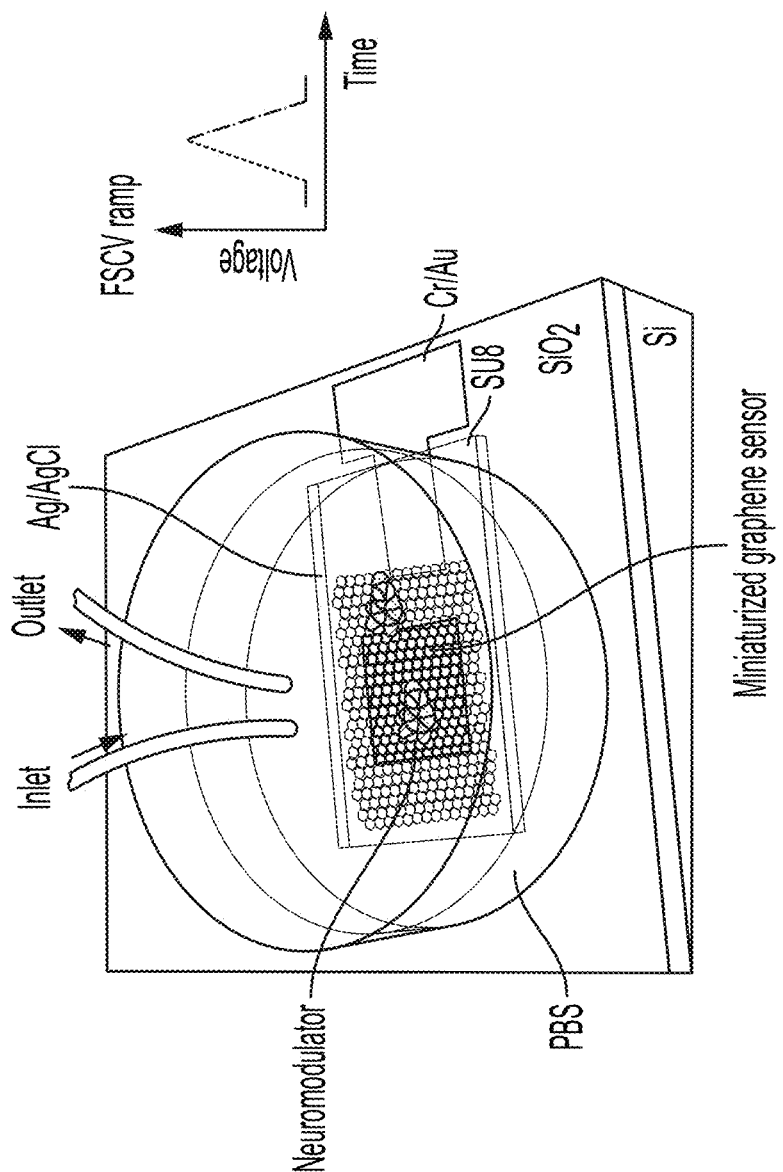
FIG. 1A illustrates a FSCV experimental set-up that contains a multilayer graphene (MLG) electrode of the present disclosure.

The present disclosure will now be described in greater detail by referring to the following discussion and drawings that accompany the present disclosure. It is noted that the drawings of the present disclosure are provided for illustrative purposes only and, as such, the drawings are not drawn In the following description, numerous specific details are set forth, such as particular structures, components, materials, dimensions, processing steps and techniques, in order to provide an understanding of the various embodiments of the present disclosure. However, it will be appreciated by one of ordinary skill in the art that the various embodiments of the present disclosure may be practiced without these specific details. In other instances, well-known structures or processing steps have not been described in detail in order to avoid obscuring the present disclosure.

Engineered structures, particularly, carbon-based electrodes, with enhanced sensitivity are disclosed. Notably, carbon-based electrodes with arbitrary sensitivity can be manufactured with high reliability and homogeneity utilizing certain physical principles as described herein. Specifically, one can engineer the sensitivity of carbon-based electrodes by changing the density of $sp^2$ type defects present in a multilayer graphene (MLG) film. In accordance with the present disclosure, the $sp^2$ type defects consist of point and line defects. The term "multilayer graphene film" denotes graphene crystals that are vertically stacked one atop the other. Each graphene crystal (and thus each graphene layer) contains a two-dimensional chain of aromatic carbon rings. Thus, and stated another way, the present disclosure provides carbon-based electrodes composed of a vertical stack of graphene crystals, wherein each graphene crystal of the vertical stack contains two-dimensional chains of aromatic carbon rings in which the carbon atoms are $sp^2$ hybridized. By "$sp^2$ hybridized" it is meant that the 2s orbital of a carbon atom mixes with two of the three available $2p$ orbitals to create new hybrid orbitals that form chemical bonds between atoms (e.g., between carbon atoms in graphene).

The number of graphene crystals (i.e., layers of graphene) that are present in the vertical stack is at least one. In some embodiments, it is preferred that the number of graphene crystals (i.e., layers of graphene) in the vertical stack is larger than 2, referred to as multilayer graphene (MLG). The graphene crystals in the vertical stack are locally parallel to each other.

The carbon-based electrodes have engineered $sp^2$ type defects (i.e., $sp^2$ hybridization). By "engineered $sp^2$ type defects" it is meant that $sp^2$ type defects are intentionally induced into a MLG film. In one embodiment, the carbon-based electrodes of the present disclosure can be formed by first forming MLG film devoid of any engineered $sp^2$ type defect sites. MLG films devoid of any engineered $sp^2$ type defect sites can be formed utilizing techniques well known to those skilled in the art. Next, the engineered $sp^2$ type defect sites are intentionally introduced into to the multilayer graphene film that is devoid of any engineered $sp^2$ type defect sites.

In one embodiment, introducing the engineered $sp^2$ type defect sites into to the multilayer graphene film that is devoid of any engineered $sp^2$ type defect sites may be achieved by introducing ions to the multilayer graphene film which are larger than carbon atoms. Examples of such ions that can be used to intentionally introduce engineered $sp^2$ type defect sites into the multilayer graphene film that is devoid of any engineered $sp^2$ type defect sites may include, but are not limited to, argon and xenon. In some embodiments, the introducing ions may include ion implantation or a plasma-assisted method. In some embodiments, the density of the engineered $sp^2$ type defects can be controlled by selecting an energy and dose of the ions. In one example, the energy used to introduce the ions into the MLG film can be from 80 eV to 10 keV, and the dose of the ions can be from $1\times10^{10}$ atoms/cm$^2$ to $5\times10^{14}$ atoms/cm$^2$. Other ion doses and energies can be used to introduce the engineered $sp^2$ type defect sites into the MLG film. In some embodiments, and to introduce $sp^2$ type defects uniformly through the entire width of an MLG film, multiple implantations at different energies can be used. In some embodiments, irradiated graphene films can be stacked to form thicker MLG films.

Following the introduction of the engineered $sp^2$ type defect sites into the multilayer graphene film that is devoid of any engineered $sp^2$ type defect sites, the resultant engineered MLG film can be subjected to an annealing process that can either remove possible carbon-carbon $sp^3$ type defects from the resultant engineered MLG film or further tune the density of the desired point defects produced by irradiation. The annealing may be performed in vacuum or in an inert ambient gas such as, for example, helium and/or argon. The annealing may be performed at a temperature from 200° C. to 1600° C. and for a duration from 5 seconds to 300 minute. Other annealing temperatures and/or times may be used. For higher annealing temperatures and/or times, a greater density of defects can be removed from the resultant engineered MLG film. In some embodiments, the annealing process is designed to remove all possible carbon-carbon $sp^3$ defects from the resultant engineered MLG film.

In another embodiment, the carbon-based electrode of the present disclosure can be provided by first forming an amorphous carbon film. The amorphous carbon film (which lacks any large range order of crystal structure) can be formed by a deposition process such as, for example, sputtering or evaporation. In some embodiments, the amorphous carbon film can be derived from a polymeric film. After forming the amorphous carbon film, an annealing process is employed. In some embodiments, and prior to annealing, a metal catalyst can be formed on the amorphous carbon film. The metal catalyst that can be used in the present disclosure includes, but is not limited to, nickel (Ni), cobalt (Co) or copper (Cu). The metal catalyst can be formed by utilizing a deposition process such as, for example, plating or sputtering. The metal catalyst may have a thickness from 2 nm to 200 nm.

In either embodiment, annealing is then performed to convert the amorphous carbon film into a MLG film containing engineered $sp^2$ type defects. This annealing may be performed in vacuum or under an inert ambient such as helium and/or argon. In one embodiment, the annealing can be performed at a temperature greater than 900° C. In another embodiment, the annealing can be performed at a temperature from 600° C. to 1600° C. In some embodiments in which no metal catalyst is employed, the annealing can be performed at a temperature above 1600° C. In some embodiments, the annealing can be designed to remove $sp^a$ carbon-carbon defects from the resultant engineered MLG film.

After providing the carbon-based MLG films with engineered $sp^2$ type defects, the MLG films can be patterned into a desired electrode shape and size utilizing existing nanopatterning processes that are compatible with silicon based technologies. That is, the MLG films can be patterned into a desired electrode shape and size utilizing lithography and etching. In one example, the patterning may be performed utilizing electron-beam lithography.

The engineered carbon-based electrodes of the present disclosure can be used as a passive sensing element in electrochemistry. In some embodiments, the engineered carbon-based electrodes of the present disclosure can be used in FSCV for sub-second measurement of the concentration of dopamine molecules. In another embodiment, the engineered carbon-based electrodes of the present disclosure can be used in FSCV for sub-second measurement of the concentration of ascorbic acid. Other analytes measured with these electrodes include, but are not limited to, serotonin, norepinephrine, lactate, and adenosine.

The carbon-based electrodes containing engineered $sp^2$ type defects of this disclosure have unprecedented sensitivity compared with existing carbon-based electrodes not containing engineered $sp^2$ type defects. The methods of the present disclosure, which are used to provide carbon-based electrodes containing engineered $sp^2$ type defects, reduce variance of sensitivity across batches of electrodes, creating arrays of homogeneous carbon-based electrodes for use in sensing applications where such homogeneity is crucial, including measurement of analytes in biological tissues.

In some embodiments and, in order to functionalize the carbon-based electrode of the present disclosure to respond as a sensor, a biological functionalization material can be applied to the surface of the MLG film that provides the carbon-based electrode of the present disclosure. In some embodiments, the carbon-based electrode of the present disclosure can be used without applying a biological functionalization material thereto. When present, the biological functionalization material can be applied to the MLG film either prior to, or after formation of the carbon-based electrode. By "biological functionalization material" it is meant any bioreceptor that binds with a complementary target biomolecule to create a binding event. In some embodiments, biochemical reactions involving the biological functionalization material generate an electrical signal which can be conducted by the carbon-based electrode under an applied electric potential. Examples of biological functionalization materials that can be used in the present disclosure include an oligonucleotide, a nucleic acid, a peptide, a ligand, a protein, an enzyme, or any other material apt to bind with a complementary target biomolecule. The biological functionalization material can be applied to the MLG films utilizing established biological functionalization processes known to those skilled in the art. Such biological functionalization processes typically include a series of chemical reactions that attach the biological functionalization material on the surface of the electrode structure.

The carbon-based electrode containing MLG having engineered $sp^2$ type defects can be used as a component in various sensors including biosensors which include other well-known components, such as, but not limited to, reference and counter electrode structures. The carbon-based electrode containing MLG having engineered $sp^2$ type defects can be also used with active charge-based sensors such as, for example, field-effect transistor sensors. Sensors containing the carbon-based electrode of the present disclosure can be used in electrochemical measurement applications. For example, the carbon-based electrode containing MLG having engineered $sp^2$ type defects can be used in voltammetry or amperometry to determine the concentration of an analyst such as dopamine or ascorbic acid.

The carbon-based sensor including an electrode composed of multilayer graphene having engineered $sp^2$ type defects can be used for electrochemical analysis of a targeted analyte. The term "analyte" is used to refer to a substance or chemical constituent such as a biological fluid (for example, blood, interstitial fluid, cerebral spinal fluid, lymph fluid, or urine) that can be analyzed, in vivo or in vitro. Analytes can include naturally occurring substances, artificial substances, metabolites, and/or reaction products. In some embodiments, the analyte is dopamine or ascorbic acid. However, other molecules, including, but not limited to lactate, salts, sugars, proteins, fats, vitamins, and hormones naturally occurring in the blood or interstitial fluids can constitute analytes in certain embodiments. The analyte can be naturally present in biological fluid or endogenous; for example, a metabolic product, a hormone, and antigen, and an antibody. Alternatively, the analyte can be introduced into the body or exogeneous, for example, a contrast agent for imaging, a radioisotope, a chemical agent, a ceutical composition including, but not limited to insulin. The metabolic products of drugs and pharmaceutical compositions are also contemplated as analytes.

The electrochemical analysis of the targeted analyte includes contacting the targeted analyte with a carbon-based sensor including the electrode composed of multilayer graphene having engineered $sp^2$ type defects. In some embodiments, the analyte is present in a human or animal body. Next, a signal generated by an electrochemical reaction of the targeted analyte at the surface of the carbon-based electrode is detected by utilizing detection means that are well known to those skilled in the art.

In the present disclosure, and in yet another embodiment, neurochemical measurements in real time are employed to reveal the physical principle that underlies the electrode sensitivity in carbon nanomaterials. In the present disclosure, MLG films, as defined below, are employed due to (i) their important technological relevance, and (ii) ease of defect engineering. In the present disclosure, the MLG films have different amounts of zero-dimensional defects and one-dimensional defects, quantified using Raman spectroscopy. Zero-dimensional defects often referred to as "point defects" or "point-like defects" include for example, vacancies. One-dimensional defects often referred to as line defects include, for example, crystallite borders or misfit dislocations. In some embodiments, an average spacing between point defects within each graphene layer ranges from 5 nm to 1μm. In other embodiments, the sensitivity of the MLG films may increase with decreasing spacing between point defects. In yet another embodiment, the density of point defects in the constituent graphene layers is nearly similar.

In the present disclosure, miniaturized electrodes are fabricated from these MLG films by utilizing nanofabrication techniques well known to those skilled in the art, and their response to dopamine and serotonin molecules has been examined. It has been determined that the area-normalized sensitivity of the MLG electrodes is amplified in proportion to the density of zero-dimensional defects and is independent of the crystallite size. By increasing the density of zero-dimensional defects, the MLG electrodes of the present disclosure can achieve a remarkably high area-normalized sensitivity of about 170 $pA \cdot \mu m^{-2} \cdot \mu M^{-1}$ in response to dopamine.

Once the zero-dimensional defect density exceeds a threshold value, which indicates the onset of transition to a fully disordered $sp^2$ carbon material, as discussed herein below, the electrode sensitivity decreases rapidly. By analyzing the surface chemical properties of several MLG electrodes with markedly different sensitivity values, it has been determined that there is no direct correlation between the density of oxygen-containing functional groups and the electrode sensitivity. These findings provide a powerful practical guide for constructing miniaturized electrochemical sensors with homogeneous properties and predictable sensitivity from $sp^2$ carbon films.

The MLG films of the present application may contain 1-dimensional defects, whose density can be quantified using $L_a$. The MLG films of the present disclosure may also contain from about $10^{10}$ zero-dimensional defects/$cm^2$ to about $10^{13}$ zero-dimensional defect/$cm^2$. In one embodiment, the zero-dimensional defect density range may be from about $10^{10}$ zero-dimensional defects/$cm^2$ to about 4.5 $10^{12}$ zero-dimensional defect/$cm^2$. The MLG films of the present application may be undoped, or doped with a p-type or n-type dopant. In some embodiments, the MLG film has a porous structure for increasing the total surface area. In some embodiments the MLG film comprises highly ordered multilayered graphene, characterized by large crystal size, $L_a$. In another embodiment, the MLG film comprises nanocrystalline graphite, characterized by small crystal size, $L_a$. In yet another embodiment, the MLG film comprises a MLG material between highly ordered multilayered graphene and nanocrystalline graphite. In some embodiments, the MLG film has a point-like defect density in the range of about $10^{10}$ to about $4\text{-}5\times10^{12}$ $cm^{-2}$. In another embodiment, the density of area-normalized sensitivity of the MLG electrode is linearly proportional to the average density of point-like defects. In some embodiments, the maximum area-normalized sensitivity of the MLG electrode is achieved at an average point-like defect density of about $4\text{-}5\times10^{12}$ $cm^{-2}$.

The MLG films of the present disclosure can be formed utilizing some variant of chemical vapor deposition (e.g., hot wall CVD, cold wall CVD, or plasma-enhanced CVD), by graphitization of SiC through thermal desorption of silicon, or by utilizing a metal-induced transformation of amorphous carbon. In the metal-induced transformation of amorphous carbon, an amorphous carbon film (which lacks any large range order of crystal structure) can be formed by a deposition process such as, for example, sputtering or evaporation. In some embodiments, the amorphous carbon film can be derived from a polymeric film. After forming the amorphous carbon film, a metal catalyst can be formed on the amorphous carbon film. The metal catalyst that can be used in the present disclosure includes, but is not limited to, nickel (Ni), cobalt (Co) or copper (Cu). The metal catalyst can be formed utilizing a deposition process such as, for example, plating or sputtering. The metal catalyst may have a thickness from 2 nm to 200 nm. Next, an annealing is then performed to convert the amorphous carbon film into a multilayer graphene film. This annealing may be performed in vacuum or under an inert ambient such as helium and/or argon. In one embodiment, the annealing can be performed at a temperature greater than 900° C. In another embodiment, the annealing can be performed at a temperature from 600° C. to 1600° C.

After providing the multilayer graphene film (either by CVD, metal-induced transformation of amorphous carbon, or other production methods), the multilayer graphene film can be patterned into a carbon-based electrode having a desired electrode shape and size utilizing existing nanopatterning processes that are compatible with silicon based technologies. That is, the MLG films, i.e., the multilayer graphene film, can be patterned into a desired electrode shape and size utilizing lithography and etching. In one example, the patterning may be performed utilizing electron-beam lithography.

In some embodiments and, in order to functionalize the carbon-based electrode of the present disclosure to respond as a sensor, a biological functionalization material, as defined above, can be applied to the surface of the graphitic film, i.e., the multilayer graphene film, that provides the carbon-based electrode of the present disclosure. In some embodiments, the carbon-based electrode of the present disclosure can be used without applying a biological functionalization material thereto. When present, the biological functionalization material can be applied to the MLG film of the present disclosure either prior to, or after formation of the carbon-based electrode, utilizing established biological functionalization processes known to those skilled in the art. Such biological functionalization processes typically include a series of chemical reactions that attach the biological functionalization material on the surface of the electrode structure.

The carbon-based electrode containing the MLG films of the present disclosure can be used as a component in various sensors including biosensors which include other well-known components, such as, but not limited to, reference and counter electrode structures. Sensors containing the carbon-based electrode of the present disclosure can be used in electrochemical measurement applications. For example, the carbon-based electrode containing the MLG films of the present disclosure can be used in different voltammetry or amperometry measurements to determine the concentration of an analyst such as dopamine or ascorbic acid.

The carbon-based sensor including the MLG films of the present disclosure can be used for electrochemical analysis of a target analyte, as defined above. The electrochemical analysis of the targeted analyte includes contacting the targeted analyte with a carbon-based sensor including an electrode composed of the MLG films of the present disclosure. In some embodiments, the analyte is present in a human or animal body. Next, a signal generated by an electrochemical reaction of the targeted analyte at the surface of the carbon-based electrode is detected utilizing detection means that are well known to those skilled in the art.

Example for MLG Film Embodiment

This specific example is only illustrative and by no means limiting. Various approaches exist in literature for producing multilayer graphene. To demonstrate that the findings of the present disclosure are universal and not specific to a particular production method, two types of MLG films were used: (i) multilayer graphene grown by chemical vapor deposition (CVD), and (ii) multilayer graphene produced by metal-induced transformation of amorphous carbon, as defined above.

Figures 1B, 1C:
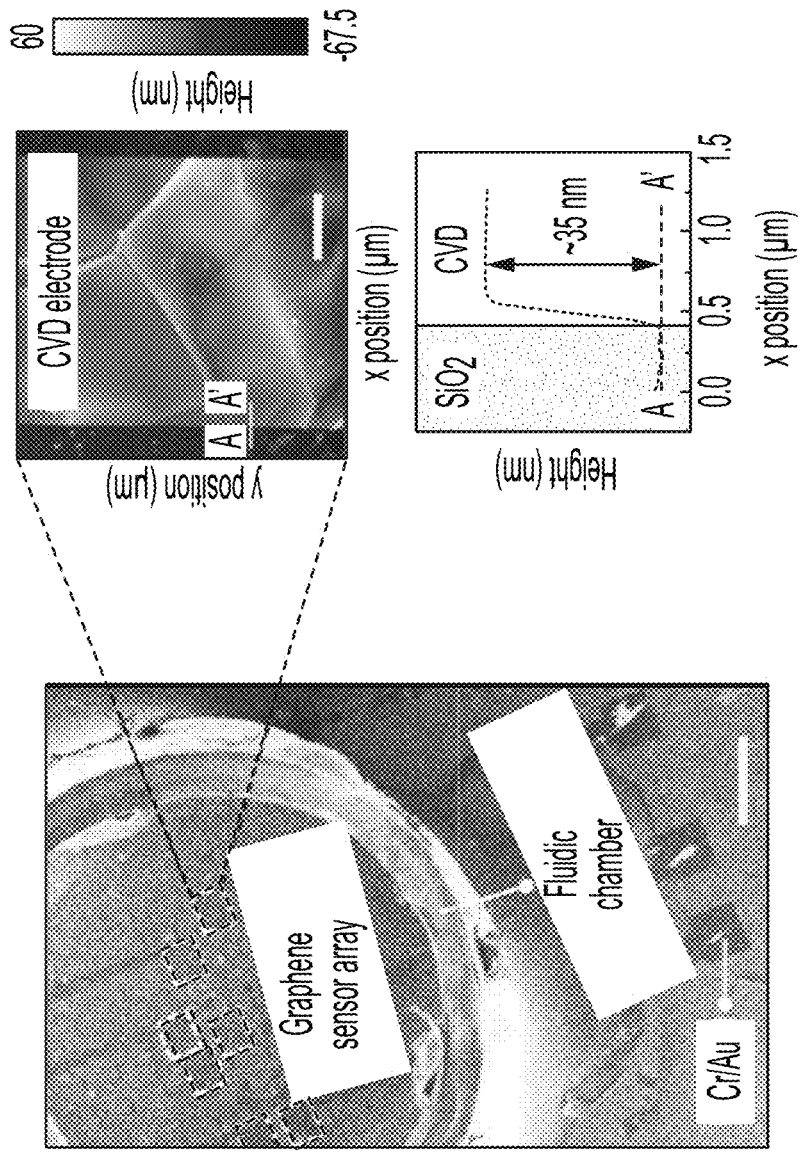
FIG. 1B is an SEM image illustrating (i) miniaturized sensors that can be built using the graphitized or chemical vapor deposition (CVD) films of the present application, and (ii) a fluidic chamber that can be mounted on the samples before FSCV measurements.
FIG. 1C is an atomic force microscopic image of an example CVD MLG electrode.

FIG. 1A illustrates a FSCV experimental set-up that was used with the MLG electrodes of the present disclosure. A similar setup was also employed for carbon fiber (CF) electrodes. In the FSCV experimental set-up shown in FIG. 1A, a MLG graphene electrode of the present disclosure is present on a surface of a silicon dioxide layer, which is formed on a silicon substrate. The MLG graphene electrode is contained within a fluidic chamber. The fluidic chamber includes an analyte. A probe composed of gold contacts a portion of the MLG electrode. The FSCV experimental set-up also included a reference electrode, an inlet conduit and an outlet conduit. FIG. 1B shows a top-view example image of a graphene sensor array taken by scanning electron microscopy (SEM).

MLG films produced using CVD typically have different amounts of $sp^2$-hybridized defects, which often stems from minor differences in production method and apparatus. MLG films produced using CVD can be obtained from commercial sources such as, for example, Graphene Supermarket, or Graphene Platform, Inc. These MLG films were grown on nickel foils and have a thickness of about 30 nm or more (FIG. 1C). To fabricate electrodes, the CVD multilayer graphene films were transferred onto $SiO_2$/Si substrates using standard chemical layer-transfer processes and then patterned into small islands using standard nanofabrication techniques well known to those skilled in the art.

In some embodiments, a method was used to controllably produce multilayer graphene with different types and amounts of structural defects. Notably, the method is based on the metal-induced graphitization of amorphous carbon using a thin nickel catalyst. In the method, patterned islands of an SU8 polymer were converted to diamond-like carbon (DLC) by annealing the samples in an Ar/$H_2$ gas mixture at 400° C. The structural properties of the MLG films made from this method sensitively depended on the nickel thickness, annealing temperature, and growth time. By tuning these parameters, guided by Raman analysis explained below, multiple samples were produced with different amounts of structural defects. These samples can be referred herein as graphitized samples. The process was performed at temperatures below 1100° C., allowing the graphitization of the DLC islands directly on $SiO_2$/Si substrates, as shown in FIG. 2A.

Figure 2B:
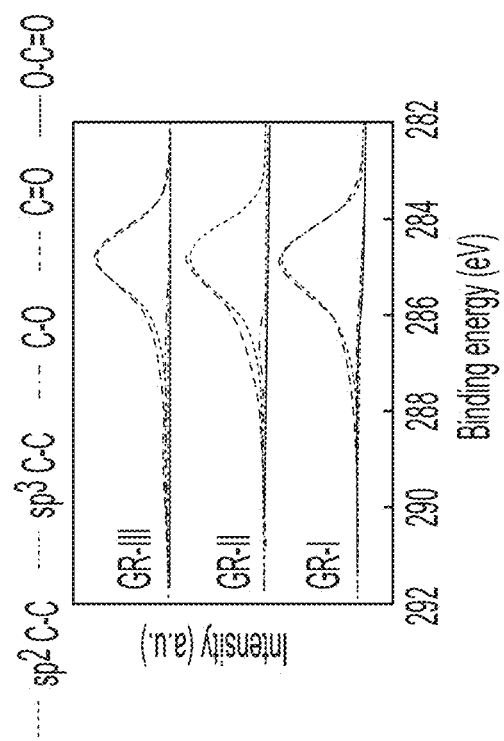
FIG. 2B shows X-ray photoelectron spectroscopy (XPS) data confirming the graphene-like nature of the films produced using metal-induced graphitization of DLC.
Figure 2A:
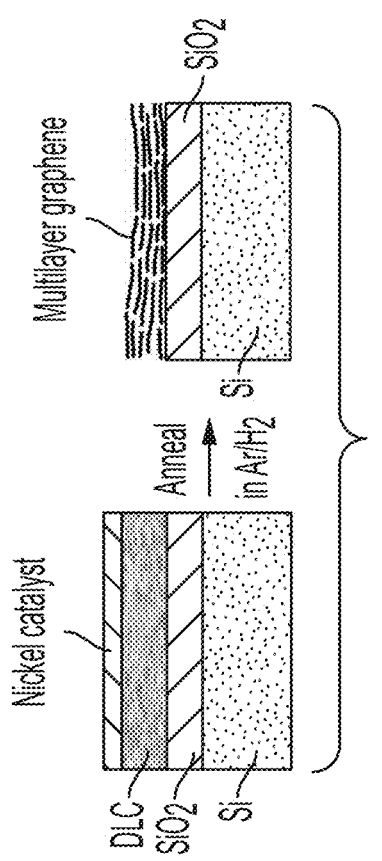
FIG. 2A illustrates a schematic for producing multiple MLG samples with different amounts of the structural defects by using metal-induced graphitization of diamond-like carbon (DLC).

FIG. 2B shows the corresponding carbon spectrum of three representative MLG films (graphitized), characterized by high-resolution X-ray photoelectron spectroscopy (XPS). The detailed analysis of the XPS data confirmed the MLG nature of these films. The ability to produce homogeneous graphitized samples with reproducible properties was one key for realizing a dense array of miniaturized electrodes.

Figure 3C:
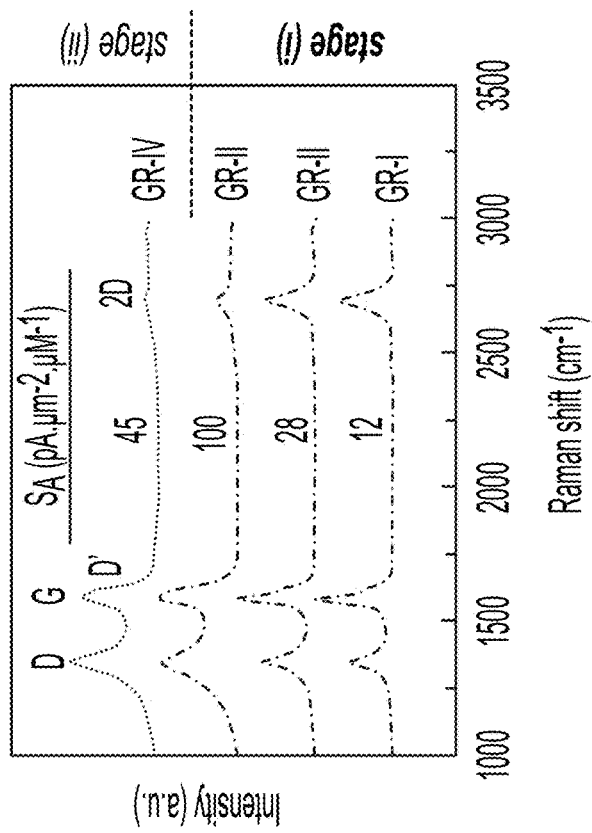
FIG. 3C shows the structural properties of graphitized films produced by metal-induced graphitization of DLC as measured by Raman spectroscopy.
Figure 3B:
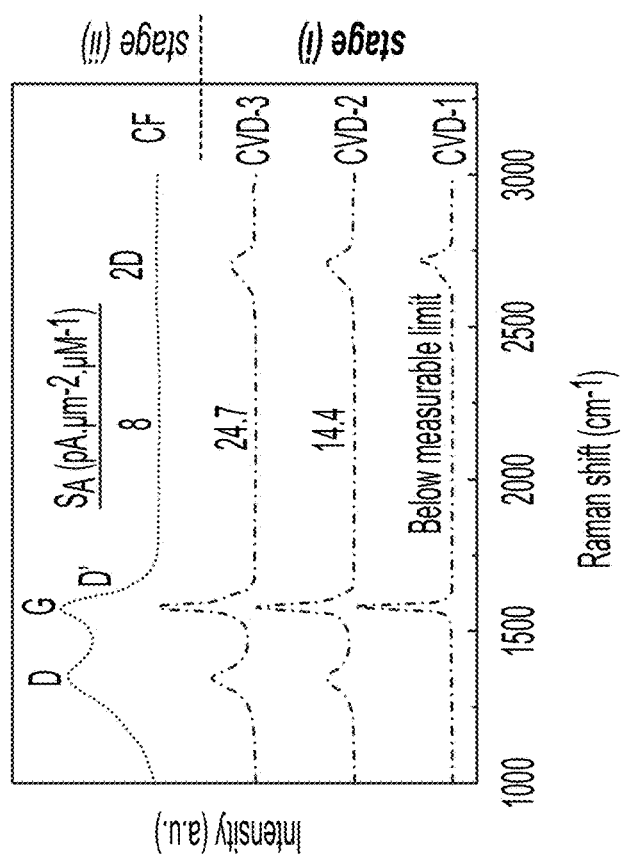
FIG. 3B shows the structural properties of CVD films as measured by Raman spectroscopy.

One simple way to classify defects in any material is based on the dimensionality of the defects. Graphene and its related structures belong to the family of two-dimensional (2-D) materials. Therefore, defects in graphene are either zero- or one-dimensional, as shown in FIG. 3A. The density of point defects (zero-dimensional) can be quantified using the average distance between the defects ($L_D$), while the density of line defects (one-dimensional) can be quantified using the average crystallite size ($L_a$). Raman spectroscopy can be used as a non-destructive method for quantifying these $sp^2$-type defects in graphene. FIGS. 3B-3C show the Raman spectra for a few example CVD and graphitized MLG films, containing different amounts of point and line defects. The Raman spectrum of an example CF electrode is also shown in FIG. 3B. The distinct peaks in the Raman spectrum of MLG films are well-studied. The G peak appears at about 1576 $cm^{-1}$ and signifies the $sp^2$ hybridization of carbon atoms. The D peak arises from the breathing modes of aromatic carbon rings and is activated by $sp^2$-hybridized defects. The 2D peak is the second-order of the D peak, which is present only in fully $sp^2$-bonded carbon materials. The evolution of the spectral line shape of these peaks in FIGS. 3B-3C (from bottom to top) illustrates the gradual transition of the film structure (i) from a highly-ordered graphene to a disordered nanocrystalline graphite and (ii) finally to a fully disordered $sp^2$ carbon film.

In stage (i), the D peak increases monotonically and 2D peak is visible in the Raman spectra. Upon transition into stage (ii), the 2D peak intensity weakens dramatically and its linewidth becomes noticeably broad. These observations are consistent with the previous reports on the amorphization trajectory of graphene.

Figure 3D:
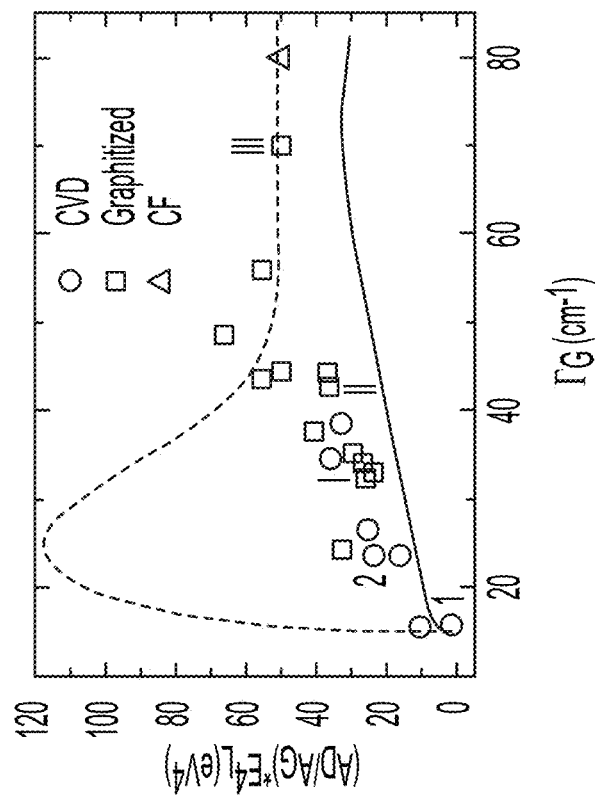
FIG. 3D illustrates the analysis of Raman data to characterize the density of point and line defects.
Figure 3E:
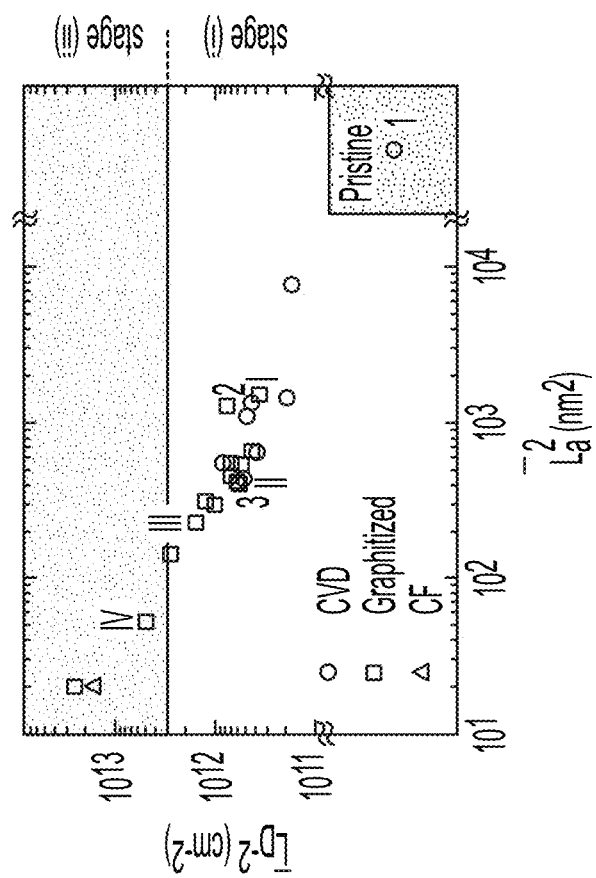
FIG. 3E summarizes the average point-like defect density ($L_D^{-2}$) v.s. the average crystallite area for multiple CVD and graphitized samples.

A recent numerical method as disclosed by Cancado, et al. "Disentangling contributions of point and line defects in the Raman spectra of graphene-related materials", 2D materials (4):025039 (2017), was applied for extracting the amounts of point and line defects from the Raman data of the CVD, graphitized, and CF samples. To do so, a plot of $(A_D/A_G) \times E_L^4$ as a function of the full-width at half-maximum (FWHM) of the G peak ($\Gamma_G$), as shown in FIG. 3D, was first performed. In this plot, the ($A_D/A_G$) is the area ratio of the D and G peaks and $E_L$ is the laser excitation energy. From the numerical simulations, the average crystallite size ($L_a$) and the average distance between point-like defects ($L_D$) for the MLG films of the present disclosure and CF samples were extracted. FIG. 3E illustrates $1/L^2_D$ as a function of $L^2_a$, where $1/L^2_D$ and $L^2_a$ represent the average point-like defect density and the average crystallite area. The plot indicates that these MLG films collectively covered a broad range of average line and point-like defect densities. Further, the Raman data suggest that the transition from stage (i) to stage (ii) occurs at an $L_D$ of about 5-6 nm (yellow shading).

To reveal the link between the structural defects and the electrode sensitivity, FSCV measurements was performed. Using standard nanofabrication, miniaturized MLG electrodes as shown schematically in FIG. 1A were formed. To avoid unintentional incorporation of additional defects during the electrode fabrication, in the beginning of the process, the sensing region of the electrode was covered with a thin Au layer (50 nm). Cr/Au was used to form an ohmic electrical contact to the MLG electrodes.

Figure 4:
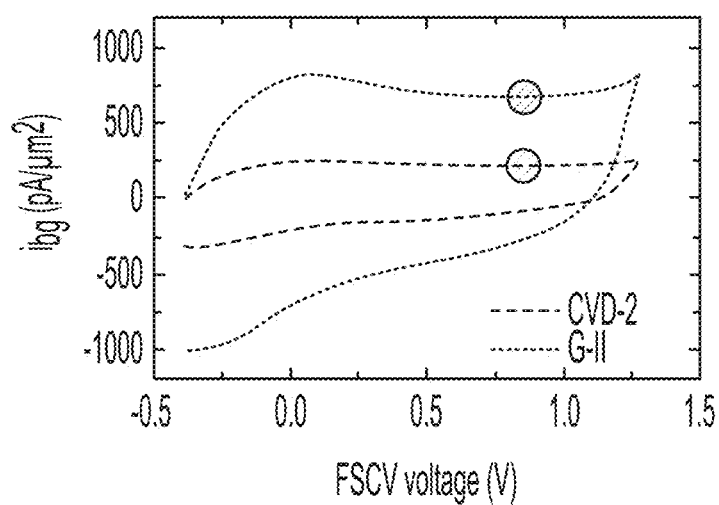
FIG. 4 shows examples of the area-normalized background current for two graphene sensors.

The sensing region of the electrodes can be accurately defined using an SU8 encapsulating layer. This layer additionally protects the metal contact from exposure to the electrolyte solution. Finally, before the measurements the protective Au layer was chemically removed and a fluidic chamber was mounted on the samples. FSCV measurements can then be performed. In some embodiments, a triangular voltage waveform can be applied to the MLG electrodes with a typical scan rate of 400 V/s. In the absence of a target molecule, the voltage waveform produces only a background current ($i_{bg}$) due to the charging and discharging of an apparent capacitance ($C_{ap}$) at the interface between the electrode and the electrolyte solution. In the example measurements in the present disclosure, the electrolyte was a 1×PBS solution. In FIG. 4, the background current characteristics of two example MLG electrodes are illustrated.

Figures 5A, 5B:
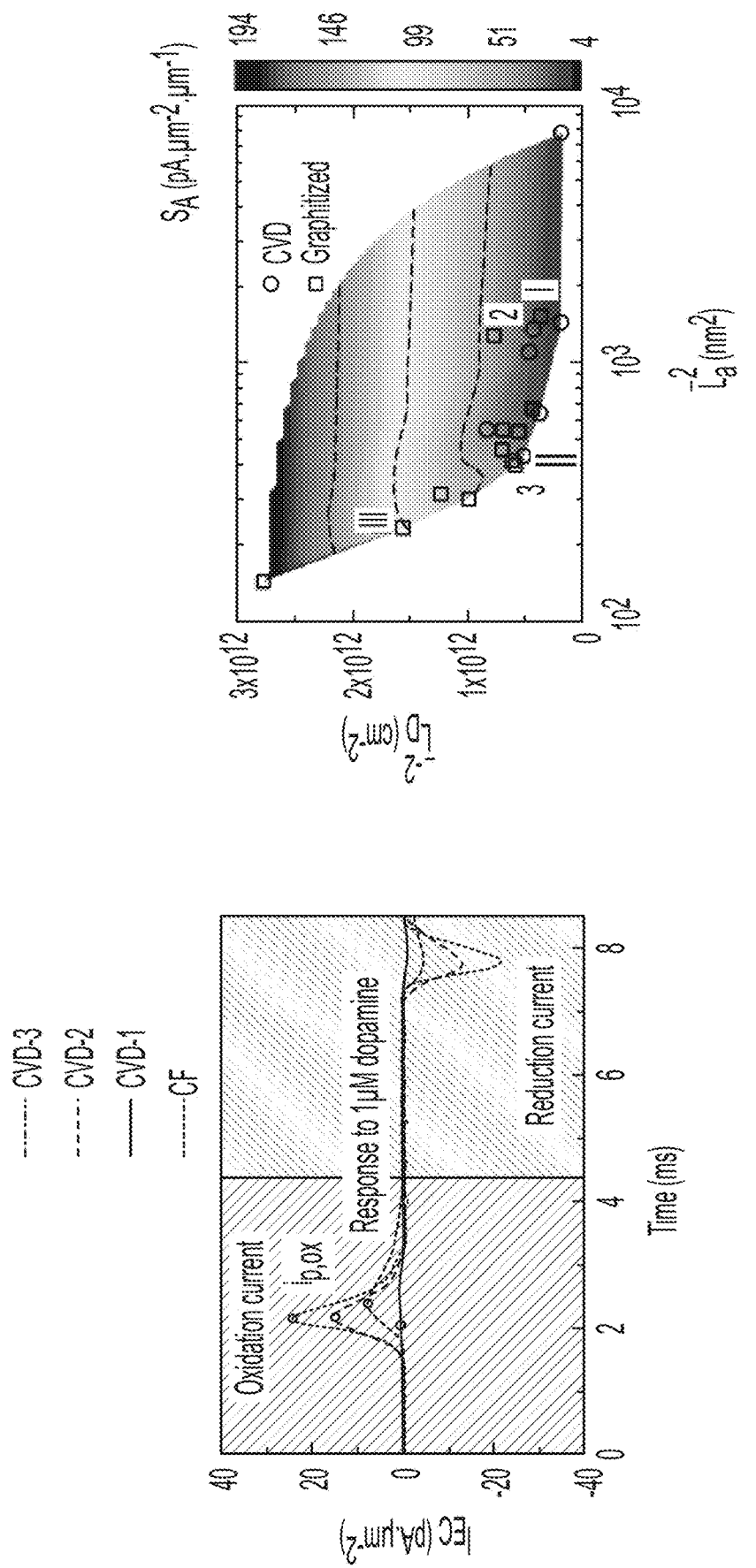
FIG. 5A illustrates a representative background-subtracted current in response to 1 µM dopamine neuromodulators in phosphate buffer saline (PBS) solution for four different electrodes made from CVD multilayer graphene and carbon fibers (CF).
FIG. 5B shows a contour plot illustrating that the area-normalized electrode sensitivity ($S_A$) of sensors made from MLG films in stage (i) of the amorphization trajectory has no dependence on the crystallite size, $L_a$, but is a strong function of point-like defect density in the film.
Figure 5C:
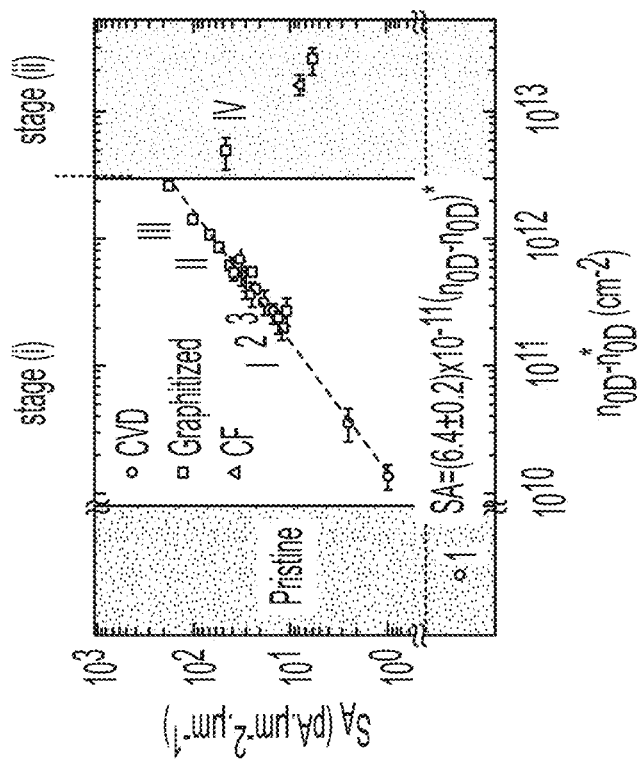
FIG. 5C is a plot of $S_A$ v.s. the average density of point-like defects illustrating the linear relation between the area-normalized electrode sensitivity and the average density of point-like defects, when the electrode material is in stage (i) of the amorphization trajectory. The sensitivity decreases rapidly as the MLG films transitions into stage (ii) of the amorphization trajectory.

To uncover the connection between the defects and the electrode sensitivity, dopamine—an important neuromodulator for action-selection and reward-motivated behavior—was used. To benchmark the neurochemical response of the MLG electrodes of the present disclosure, electrodes from conventional carbon fibers were fabricated and tested to provide a baseline. By applying a voltage ramp to the electrode, as shown in FIG. 1A, dopamine molecules first undergo an oxidation during the ramp-up, producing dopamine-o-quinone (DOQ) molecules and two free electrons. The amplitude of the current due to this charge transfer is a measure of the dopamine concentration. During the ramp-down, the DOQ molecules are subsequently reduced back to dopamine while consuming two free electrons. In FSCV, the background current is stable and always present. Hence, to determine the amplitude of the redox current, the background current is subtracted from the total FSCV current, referred to as the background subtracted current. Background subtracted current characteristics of the MLG films of the present disclosure and CF sensors were obtained in response to a 1 µM dopamine solution in PBS. The peak oxidation current measured at 1 µM defines the electrode sensitivity. This value is similar to the slope of the linear fit to the calibration curves measured at different dopamine concentrations. FIG. 5A shows the examples of the area-normalized background subtracted current for four electrodes (three MLG and one CF). This plot highlights the strong dependence of the electrode sensitivity on the structural properties of the electrode. To reveal the effect of defects on MLG sensors in stage (i), in FIG. 5B the contour plot of the area-normalized electrode sensitivity, $S_A$, as a function of the average crystallite area and the average point-like defect density is presented. From this plot, it was determined that electrodes with similar density of point-like defects and regardless of their crystallite size exhibit nearly similar area-normalized sensitivity. On the other hand, it was observed that the electrode sensitivity is amplified with increasing the average density of point-like defects. To better understand this phenomenon, $S_A$ for dopamine as a function of the average point-like defect density was plotted, as shown in FIG. 5C. The data indicated a linear increase of the sensitivity of the MLG electrodes in the stage (i) of the graphene amorphization trajectory. FSCV experiments using another analyte, serotonin, yielded similar results, confirming that linear increase of the electrode sensitivity is inherent to the electrode itself, not a property of analyte. The area-normalized sensitivity, however, departs from this trend at $L_D$ of about 5-6 nm, which corresponds to the transition into stage (ii), which indicates the onset of transition to a fully disordered $sp^2$ carbon material. FIG. 5C illustrates the sharp decrease of the electrode sensitivity in this regime. This plot explains the fundamentally lower sensitivity of the conventional CF electrodes compared to our engineered electrodes.

The results presented in FIG. 5C present two main strategies for producing electrode materials that can achieve a maximum sensitivity. First, start with an MLG film that is in stage (i) of the amorphization trajectory and directly tune its density of point defects. Second, start with a fully disordered carbon and convert it to an MLG film with maximum amounts of point defects before the material transitions into the stage (ii). An example process for the implementation of the latter strategy is to anneal such films at elevated temperatures above 1600° C. These annealing temperatures are known to remove the $sp^3$ carbon-carbon bonds and convert the film into a fully $sp^2$ carbon material.

Figure 6:
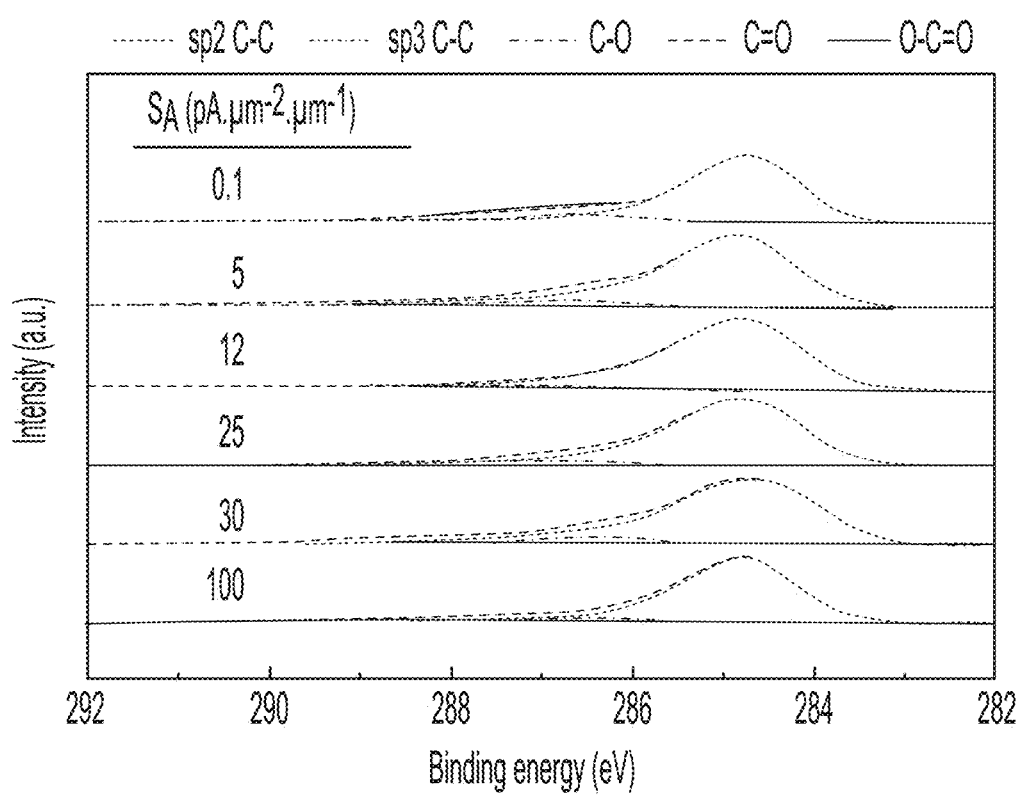
FIG. 6 is a plot illustrating the role of oxygen-containing functional groups on electrode sensitivity. XPS was used to analyze the surface chemistry of multiple electrodes with different $S_A$.

Next, the effect of oxygen-containing functional groups on the sensitivity of the MLG electrodes of the present disclosure was evaluated. Previous studies have suggested a direct correlation between the electrode sensitivity and the amounts of oxygen functional groups that are available on the surface of the carbon electrode. To evaluate the role of the oxygen functional groups, XPS measurements on multiple MLG electrodes with vastly different area-normalized sensitivity were performed. The electrodes were chosen from both CVD and graphitized samples and the measurements were performed immediately after the FSCV experiments. By analyzing the XPS data, shown in FIG. 6, the direct role of oxygen functional groups in amplifying the sensitivity of the MLG electrodes of the present disclosure was dismissed. Based on the above, two guiding principles for the design of electrochemical sensors from MLG films are provided. First, the MLG material must be in stage (i) of the graphene amorphization trajectory. Second, to achieve the highest area-normalized sensitivity for the electrode, i.e., amplifying the redox current, the concentration of point-like defects must be maximized without departing from stage (i).

The above quantitative principles would allow the implementation of sensor systems consisting of a large number of miniaturized defect-engineered MLG sensors. These sensors feature high sensitivity that are homogeneous across the sensor array. For some applications, however, the sensors may need to be transferred onto a second substrate that is different from the growth substrate. This requirement arises from the high growth temperature of MLG, which is incompatible with plastic substrates (for flexible sensing applications) or with CMOS integrated circuits (for lab-on-a-chip applications).

A scalable and efficient method for transfer of miniaturized engineered graphene onto any arbitrary substrate is now discussed in greater detail. The disclosed method involves two steps. First, the defect-engineered graphene is synthesized on two-dimensional hexagonal boron nitride (h-BN) islands. Second, those graphene-BN assemblies are then placed onto predefined regions of an arbitrary substrate using a stamp-assisted pick-and-place technique. Recent advances in the development of automated pick-and-place tools with applications in hybrid flexible electronics make this technique a compelling choice for an industrial-scale adaptation of the disclosed approach.

The disclosed approach is based on two key properties of the layered h-BN: (i) its excellent chemical stability at high temperatures, where graphene synthesis will take place, and (ii) its weak adhesion to the underlying substrate through a van der Waals force.

Figure 7A:
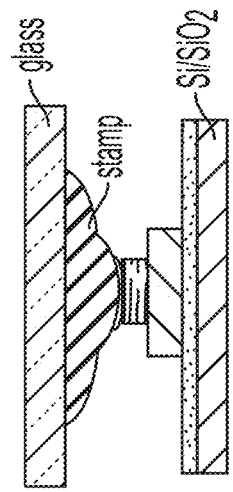
FIG. 7A is the schematic of engineered MLG growth on hexagonal boron nitride (h-BN).
Figure 7B:
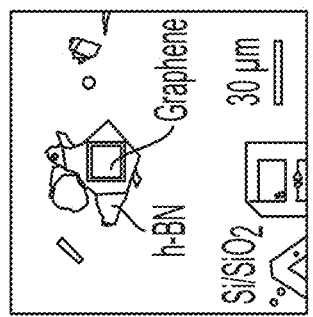
FIG. 7B is the optical image of example engineered MLG on h-BN islands.
Figure 7C:
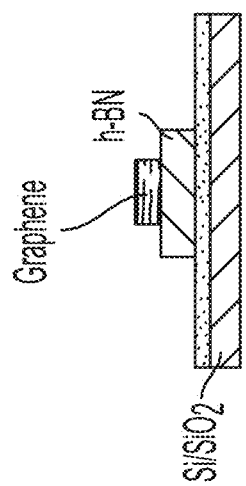
FIG. 7C illustrates the concept of the stamp-assisted transfer, when the polymeric stamp comes into contact with the graphene-BN assembly.
Figure 7D:
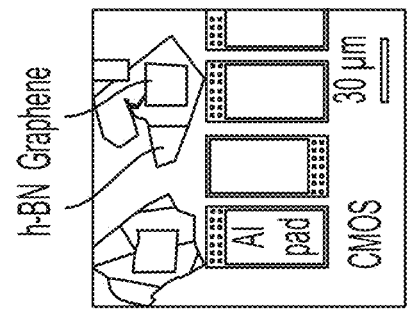
FIG. 7D illustrates the transfer process, when graphene-BN was detached from the surface.
Figure 7E:
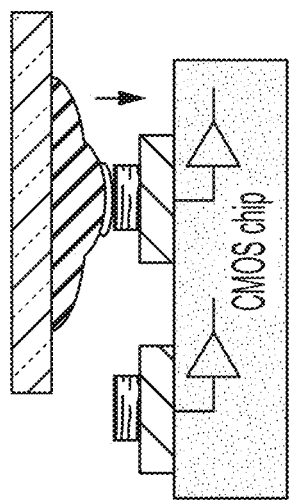
FIG. 7E shows the schematic of the graphene-BN assembly after the placement process.
Figure 7F:
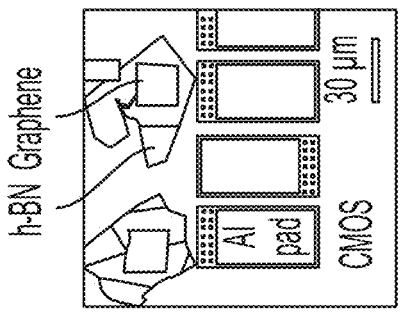
FIG. 7F is the optical image of two example graphene-BN islands transferred onto a CMOS chip.

The quantitative relationships between the sensitivity and the structural properties of graphene will guide the development of the graphene synthesis process to reliably and accurately achieve the desired sensitivity. In one embodiment, the nickel-induced transformation of amorphous carbon was used, due to the simplicity of its process, for defect engineering in graphene, as shown in FIGS. 7A-7B. The ability to use h-BN as the growth substrate, which is essential for implementing the disclosed sensor assembly process, is another advantage of this synthesis method. FIGS. 7C, 7D and 7E conceptually show the pick-and-place layer transfer process. FIG. 7F shows an example of transferred graphene sensors onto a CMOS chip using the disclosed method.

While the present disclosure has been particularly shown and described with respect to preferred embodiments thereof, it will be understood by those skilled in the art that the foregoing and other changes in forms and details may be made without departing from the spirit and scope of the present disclosure. It is therefore intended that the present disclosure not be limited to the exact forms and details described and illustrated, but fall within the scope of the appended claims.

What is claimed is:

1. A carbon-based electrode comprising:
a multilayered graphene (MLG) film having $sp^2$ hybridization, and containing a density of zero-dimensional and one-dimensional defects, wherein the density of the zero-dimensional defects is engineered to provide area-sensitivity in stage (i) of graphene amorphization trajectory that increases in a linear proportion to the average density of the zero-dimensional point defects and to provide a film structure from highly ordered multilayered graphene to disordered nanocrystalline graphite.

2. The carbon-based electrode of claim 1, wherein the film structure of the MLG film is highly ordered multilayered graphene.

3. The carbon-based electrode of claim 1, wherein the film structure of the MLG film is nanocrystalline graphite.

4. The carbon-based electrode of claim 1, wherein the film structure of the MLG film comprises a MLG material between highly ordered multilayered graphene and nanocrystalline graphite.

5. The carbon-based electrode of claim 1, wherein the MLG film is n-doped, p-doped, or undoped.

6. The carbon-based electrode of claim 1, wherein the MLG film has a point-like defect density in the range of about $10^{10}$ to about $4.5 \times 10^{12}$ $cm^{-2}$.

7. The carbon-based electrode of claim 1, wherein the maximum area-normalized sensitivity of the MLG electrode is achieved at an average point-like defect density of about $4.5 \times 10^{12}$ cm$^{-2}$.

8. The carbon-based electrode of claim 1, wherein the MLG film has a porous structure for increasing the total surface area.

9. The carbon-based electrode of claim 1, further comprising a biological functionalization material located on a surface of the MLG film.

* * * * *

UNITED STATES PATENT AND TRADEMARK OFFICE
CERTIFICATE OF CORRECTION

PATENT NO. : 11,946,895 B2  
APPLICATION NO. : 16/635634  
DATED : April 2, 2024  
INVENTOR(S) : Davood Shahrjerdi Page 1 of 1

It is certified that error appears in the above-identified patent and that said Letters Patent is hereby corrected as shown below:

In the Specification

Column 1, Lines 13-20 should read:
STATEMENT REGARDING FEDERALLY
SPONSORED RESEARCH OR DEVELOPMENT
This invention was made with government support under DE-SC0012704 awarded by the U.S. Department of Energy, R01 MH109180 awarded by the National Institutes of Health, and 1728051 awarded by the National Science Foundation. The government has certain rights in the invention.

Signed and Sealed this  
First Day of April, 2025

Coke Morgan Stewart  
*Acting Director of the United States Patent and Trademark Office*